(12) United States Patent
Brookshire et al.

(10) Patent No.: US 6,169,962 B1
(45) Date of Patent: *Jan. 2, 2001

(54) SYSTEMS AND METHODS FOR CONTROLLING GAS FLOW FROM LANDFILLS

(75) Inventors: Ronald L. Brookshire, El Cajon; Donald Brookshire, Descanso; Travis Brookshire, El Cajon; Seyed Mohammed Reza Kalantar-Nejad, El Cajon; James Joseph Beach, El Cajon, all of CA (US)

(73) Assignee: Landfill Gas & Environmental Products, Inc., El Cajon, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/717,959

(22) Filed: Sep. 23, 1996

Related U.S. Application Data (63) Continuation-in-part of application No. 08/646,039, filed on May 7, 1996, now Pat. No. 5,616,841.

(51) Int. Cl.$^7$ .................................................. G06F 19/00
(52) U.S. Cl. .......................... 702/47; 702/50; 73/19.04; 73/19.05
(58) Field of Search .................................. 166/246, 95.1, 166/53, 250.01, 369.72, 50, 64, 268, 303, 370; 702/47, 50, 45, 51; 73/19.04, 19.05, 864.73, 152.01

(56) References Cited

U.S. PATENT DOCUMENTS

| | | | |
|---|---|---|---|
| 4,026,355 | * | 5/1977 | Johnson et al. ................. 166/246 |
| 4,444,041 | * | 4/1984 | Zison .............................. 73/19.04 |
| 4,757,709 | * | 7/1988 | Czernichow . |
| 4,844,156 |   | 7/1989 | Hesh ................................... 166/263 |
| 4,886,119 |   | 12/1989 | Bernhardt et al. ................. 166/267 |
| 4,890,672 | * | 1/1990 | Hall ................................ 166/250.01 |
| 4,946,312 |   | 8/1990 | Loock et al. ...................... 405/129 |
| 5,063,519 | * | 11/1991 | Zison ................................. 702/47 |
| 5,458,006 | * | 10/1995 | Roqueta . |
| 5,462,114 | * | 10/1995 | Catanese, Jr. ....................... 166/53 |

OTHER PUBLICATIONS

State of the Art of Landfill Gas Recovery. The Controlled Landfill Project, Phase II. By Emcon Associates, 90 Archer Street, San Jose, CA 95112, prepared for Argonne National Laboratories, PG&E Co., and Southern California Gas Co. pp. 71–78. Feb. 1981.

* cited by examiner

*Primary Examiner*—James F. Trammell
*Assistant Examiner*—Cuong H. Nguyen
(74) *Attorney, Agent, or Firm*—John L. Rogitz (57) ABSTRACT

An automated, computer-controlled landfill gas recovery system includes a number of equipment vaults, with each vault being associated with one or more wells in the landfill. The wells are in fluid communication with a piping system located in the associated vault, with the piping system including a main pneumatic control valve that can be adjusted to establish gas flow rate through the well or wells. Also, each vault includes a shielded enclosure that holds sensors and a local vault controller for generating signals representative of flow rate, vacuum, and oxygen/methane/carbon dioxide content of the gas being extracted from the well. These signals are sent to a remote computer. Based on the signals generated by the sensors, the computer communicates with each vault controller to control the pneumatic control valve of each vault to establish a gas flow rate from the associated well as appropriate to accord with one of several user-selected process control regimes.

19 Claims, 5 Drawing Sheets

SYSTEMS AND METHODS FOR CONTROLLING GAS FLOW FROM LANDFILLS

This application is a continuation in part of and claims priority from U.S. patent application Ser. No. 08/646,039, filed May 7, 1996, now U.S. Pat. No. 5,616,841.

FIELD OF THE INVENTION

The present invention relates generally to landfills, and more particularly to systems and methods for controlling gas flow from landfills.

BACKGROUND

Waste products decompose in landfills, and after the free oxygen in the landfill is depleted, the waste product decomposition generates methane gas. It is desirable to recover this methane gas for environmental and safety reasons, and because subsequent to recovery the gas can be used as a source of energy.

Accordingly, systems have been developed to extract the methane. One such system is disclosed in U.S. Pat. No. 4,026,355 to Johnson et al. As contemplated by Johnson et al., several wells are sunk vertically into a landfill, and gas seeps into the wells. A vacuum pump is in fluid communication with the wells to evacuate gas from the landfill.

As recognized by Johnson et al., as gas is evacuated from a landfill, oxygenated air can seep back in if gas pressure in the landfill near the surface is lower than atmospheric pressure. The inflow of oxygenated air, however, adversely affects the generation of methane. Accordingly, Johnson et al. teaches a trial and error method of establishing a maximum gas extraction rate while ensuring that landfill gas pressure near the surface remains about equal to atmospheric pressure. Johnson et al. contemplates that the gas extraction rate is established by appropriately establishing the speed of the vacuum pump.

Unfortunately, Johnson et al. cannot be used to control the gas flow rate through individual wells independently of the other wells, because Johnson et al. contemplates controlling only overall flow rate from the landfill by means of a single vacuum pump. As recognized by the present invention, however, gas production can vary throughout a landfill. Consequently, the present invention recognizes that it is sometimes desirable to control the flow rate on a well-by-well basis.

Additionally, the degree of flow rate control afforded by Johnson et al. is relatively coarse, in that the speed of a vacuum pump typically cannot be adjusted in fine increments. As recognized herein, it is desirable to afford a relatively fine degree of flow rate control, to optimize the extraction of methane while avoiding the seepage of air into a landfill.

Moreover, the present invention recognizes, as Johnson et al. does not, that under some circumstances it might be desirable to establish a particular flow rate in response to variables other than vacuum pressure in the landfill. Accordingly, such other variables must be measured, and flow rate established accordingly. Also, it is commonly required that many of these variables be recorded. Currently, the monitoring and recording of landfill variables is labor-intensive and must be done well-by-well. Consequently, current methods of landfill monitoring are costly and time consuming. Fortunately, the present invention recognizes that it is possible to monitor and record such variables, and in addition to control the flow rate of gas extracted from the landfill in response to the variables, without requiring labor-intensive well-by-well monitoring and control.

Accordingly, it is an object of the present invention to provide a landfill monitoring and control system for remotely monitoring and/or recording landfill variables. Another object of the present invention is to provide a landfill monitoring and control system that can control gas flow through a plurality of wells in response to gas flow variables. Still another object of the present invention is to provide a landfill monitoring and control system that can remotely control gas flow through wells in a landfill. Yet another object of the present invention is to provide a landfill monitoring and control system which is easy to use and cost-effective.

SUMMARY OF THE INVENTION

A landfill gas extraction system is disclosed for controlling the extraction of gas from a landfill that has a plurality of gas well cells, with each cell including one or more gas wells. A source of vacuum is in fluid communication with the cells. The present system includes a computer and a plurality of control valves in fluid communication with a respective cell, and each control valve is controllable by the computer for controlling gas extraction from the cell.

Preferably, for each cell, at least one sensor is provided for generating a feedback signal representative of a parameter from the group consisting of: pressure, temperature, flow rate, oxygen concentration, methane concentration, and carbon dioxide concentration. As set forth in detail below, the feedback signal is communicated to the computer and the computer controls the respective control valve in response thereto.

In the presently preferred embodiment the sensor is a flow rate sensor and the feedback signal represents flow rate through the cell. Consequently, the computer controls the respective control valve to establish a predetermined flow rate. If desired, the predetermined flow rate through each cell can be based on a predetermined landfill total flow rate. Also, in each cell a pressure sensor preferably generates a vacuum signal representative of pressure in the cell, and the computer includes computer readable code means for comparing the vacuum signal to a predetermined vacuum setpoint and controlling the control valve in response thereto.

Still further, in each cell an oxygen sensor generates an oxygen signal representative of oxygen concentration in the cell. The computer includes computer readable code means for comparing the oxygen signal to a predetermined oxygen setpoint and controlling the control valve in response thereto.

In addition to the above flow priority control structures, the present invention contemplates further controlling gas flow to minimize oxygen extraction and/or to maximize methane extraction from the landfill. Thus, the computer controls the control valve of each cell to maintain oxygen concentration below a predetermined oxygen concentration setpoint, while controlling the control valves such that the sum of the gas flow rates through all the cells is maintained within a predetermined field flow rate range. Moreover, the computer can control the control valve of each cell to cause relatively more gas to be extracted from cells having relatively high methane concentrations.

In an alternate vacuum priority control strategy, the sensor is a pressure sensor and the feedback signal represents vacuum pressure in the cell, and the computer controls the control valve of each cell to establish a predetermined vacuum pressure. In this alternate embodiment, each cell can include an oxygen extraction sensor for generating an oxygen extraction signal representative of oxygen extraction from the cell. The computer includes computer readable code means for comparing the oxygen extraction signal to a predetermined oxygen extraction setpoint and controlling the control valve in response thereto. Moreover, each cell can include a temperature sensor for generating a temperature signal representative of gas temperature in the cell, and the computer includes computer readable code means for comparing the temperature signal to a predetermined setpoint and controlling the control valve in response thereto.

Regardless of the particular gas extraction priority strategy, a respective vault is provided for holding each control valve. In accordance with the present invention, each vault includes a respective pressurized enclosure for holding the sensors of the present invention therein, with the control valve being external to the enclosure. Preferably, the control valve is a pneumatically-operated valve. Furthermore, a vault controller is disposed in the enclosure, and the vault controller is in communication with the computer. The vault controller can control its respective control valve in response to signals downloaded from the computer, such that in the event that communication between the computer and a vault controller is lost, the vault controller continues to operate its associated control valve in accordance with the logic discussed above. Still further, a solenoid valve is disposed in the enclosure and is electrically connected to the vault controller for control of the solenoid valve to selectively isolate the sensor, such that a positive pressure is maintained within the enclosure to prevent the flow of gas into the enclosure. Preferably, no electrically-powered components of the vault are located outside the enclosure.

In another aspect of the present invention, a computer program device includes a computer program storage device readable by a digital processing system. A computer program is on the program storage device, and the program includes instructions that are executable by the digital processing system for performing method steps for controlling at least one valve disposed in a landfill cell gas extraction pipe to thereby control gas extraction from the pipe. As discussed further below, the method steps include the steps of receiving a feedback signal representative of at least one of: gas pressure in the pipe, gas flow rate through the pipe, oxygen concentration of gas in the pipe, and then moving the valve in response thereto.

In still another aspect of the present invention, a digital processing apparatus is disclosed for controlling a valve in a landfill to regulate the flow of gas from the landfill through the valve. The present apparatus includes computer readable code means for receiving a feedback signal representative of at least one of: gas pressure in the pipe, gas flow rate through the pipe, oxygen concentration of gas in the pipe. Also, the apparatus includes computer readable code means for causing the valve to move in response to the feedback signal.

In yet another aspect of the present invention, a landfill is provided. The landfill includes a piping system for extracting gas from the landfill through a plurality of landfill cells, with each cell including one or more wells. The landfill also includes a computer, and, for each cell, a pneumatic control valve disposed in the cell for selectively blocking gas communication therethrough. Each cell also includes an enclosure, and a source of air for pressurizing the enclosure to prevent gas from leaking into the enclosure. Moreover, each cell includes at least one sensor disposed in the enclosure for generating a feedback signal representative of an attribute of gas in the cell. At least one solenoid valve is disposed in each enclosure and is configured for selectively establishing fluid communication between the cell and the sensor. The computer generates, in response to the feedback signal, a control signal for controlling the control valve.

The details of the present invention, both as to its structure and its operation, can best be appreciated in reference to the accompanying drawings, in which like reference numerals refer to like parts, and in which:

DETAILED DESCRIPTION OF THE PREFERRED EMBODIMENT

Figure 1:
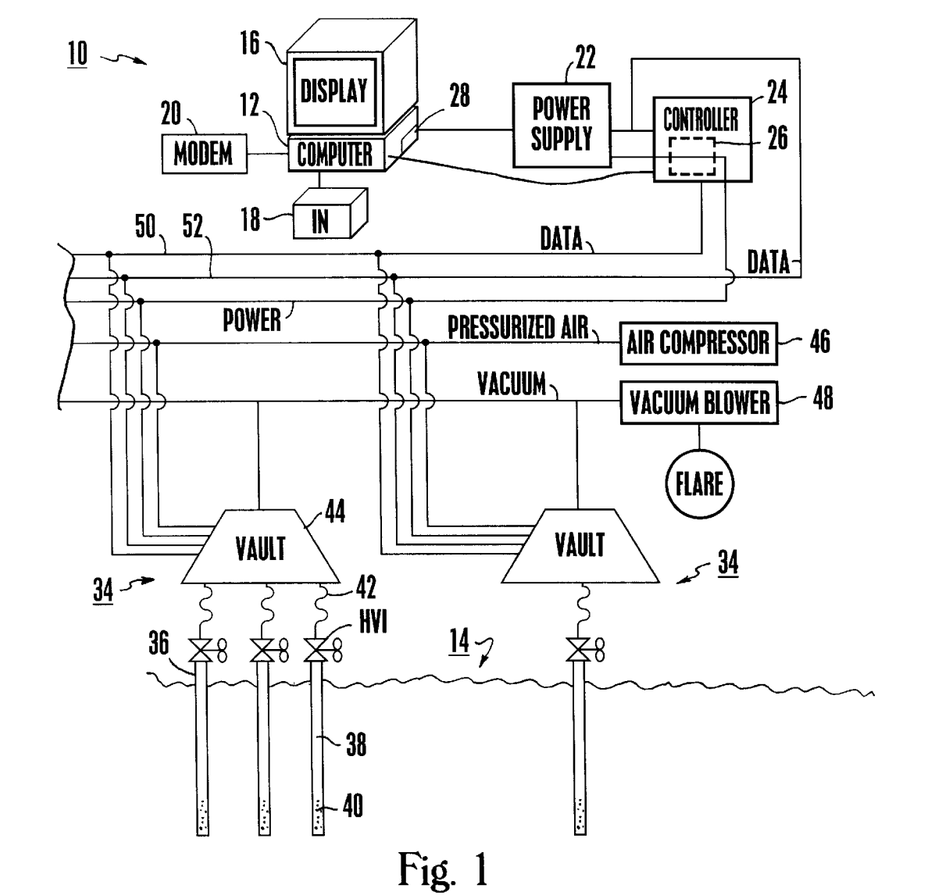
FIG. 1 is a schematic diagram of a landfill incorporating the monitoring and control system of the present.

Referring initially to FIG. 1, a system is shown and generally designated 10 for recovering methane gas from a landfill 14. As shown, the system 10 includes a computer 12 that controls the recovery of gas from a landfill, generally designated 14. In accordance with well-known principles, the computer 12 can be a personal computer (PC) having an associated man-machine interface such as a video monitor 16 and an associated input device such as a keyboard 18. The input device of the present invention, however, be a mouse, a touch screen, a ball, or other appropriate input device.

Additionally, the computer 12 can include an associated modem 20 for communicating with a computer network (not shown). As shown schematically in FIG. 1, an alternating current (ac) power supply 22 is electrically connected to the computer 12 for energizing the computer 12. Furthermore, the computer 12 is electrically connected to a field controller 24. Per the present invention, the field controller 24 is incorporated into a switchgear panel for communicating data between the computer 12 and various components located in the landfill 14, and for transferring power from the ac power supply 22 to the landfill 14 components through a power switch 26 (shown in phantom in FIG. 1).

As described in detail below, based on gas flow properties of the landfill 14, the system 10 includes a control module 28 that controls gas extraction from the landfill 14. FIG. 1 shows that the control module 28 can be included in the computer 12, but it is to be understood that the control module 28 alternatively can be implemented in each of the vault controllers described below in reference to FIG. 2.

Figure 3:
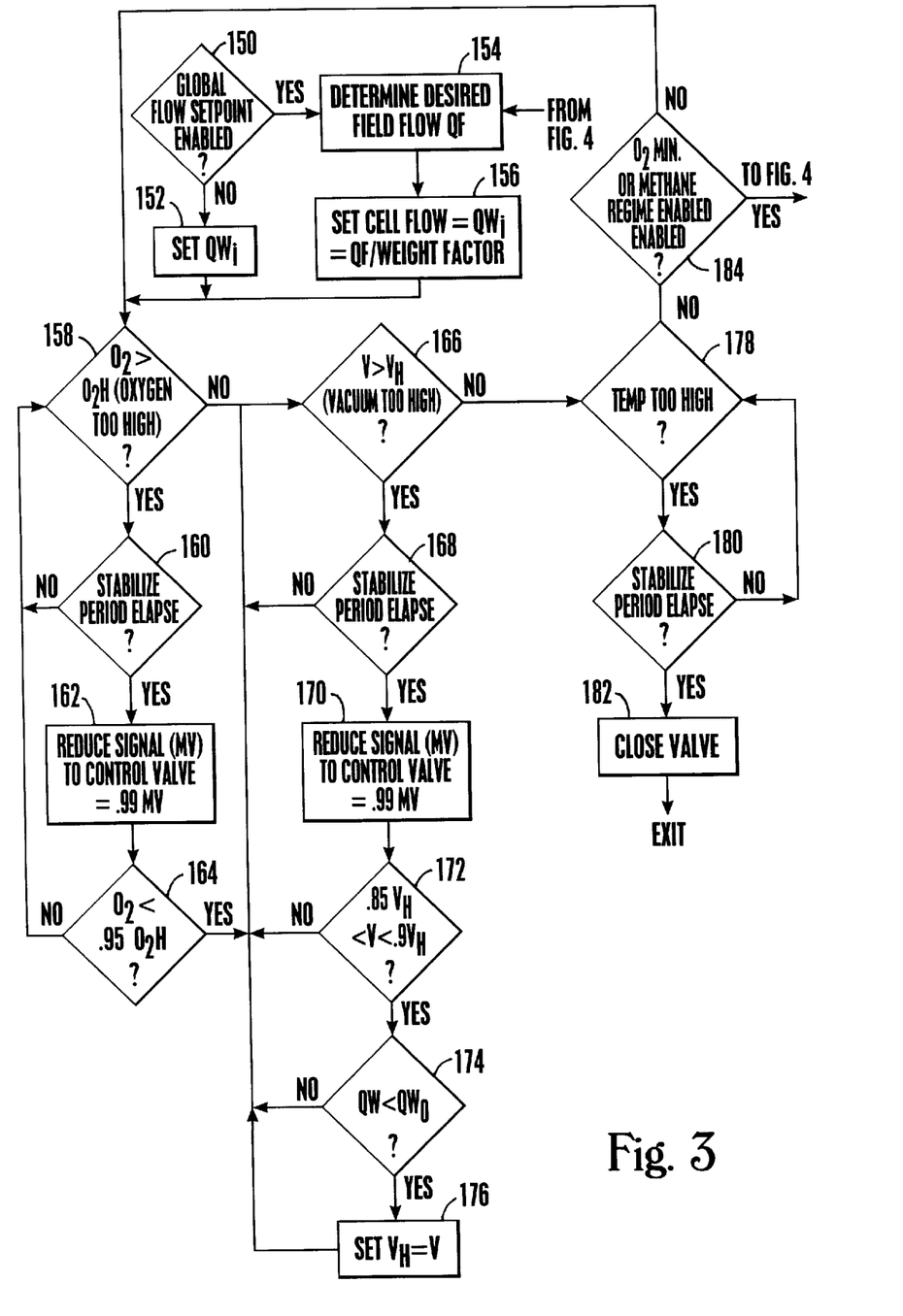
FIG. 3 is a flow chart of the flow priority control strategy of the present invention.
Figure 4:
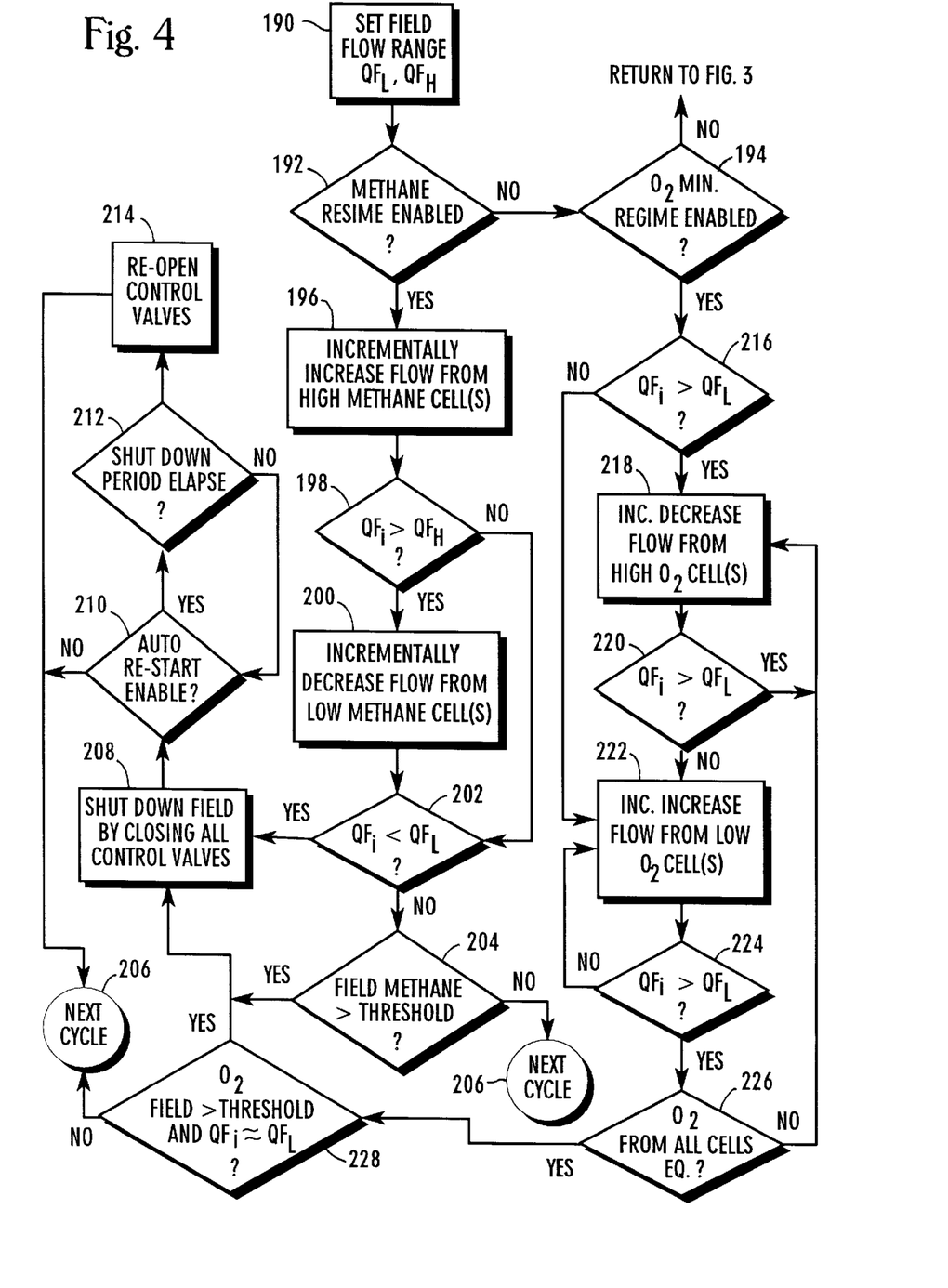
FIG. 4 is a flow chart showing the oxygen minimization and methane maximization subroutines of the flow priority control strategy shown in FIG. 3.
Figure 5:
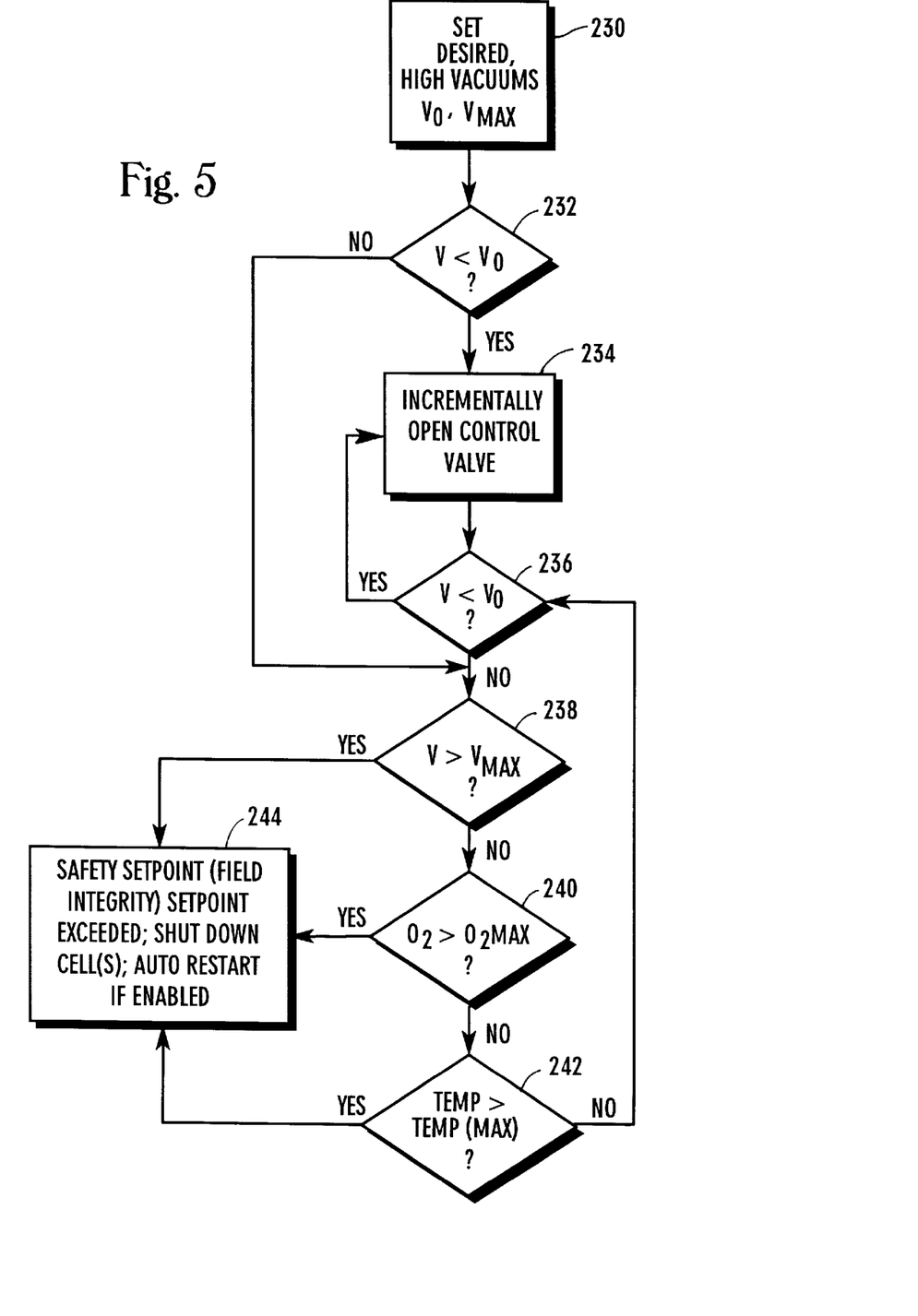
FIG. 5 is a flow chart of the vacuum priority control strategy of the present invention.

FIGS. 3–5 illustrate the structure of the control module 28 of the present invention as embodied in computer program software. Those skilled in the art will appreciate that the Figures illustrate the structures of computer program code elements that function according to this invention. Manifestly, the invention is practiced in one essential embodiment by a machine component that renders the computer program code elements in a form that instructs a digital processing apparatus (that is, a computer) to perform a sequence of operational steps corresponding to those shown in the Figures.

Figure 1A:
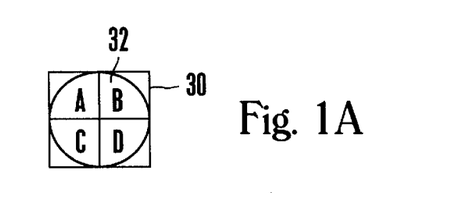
FIG. 1A shows a program storage device of the present invention.

These instructions may reside on a program storage device including a data storage medium, such as the computer diskette 30 shown in FIG. 1A. The machine component is shown in FIG. 1A as a combination of program code elements A–D in computer readable form that are embodied in a computer-usable data medium 32, on the computer diskette 30. Alternatively, such media can also be found in semiconductor devices, on magnetic tape, on optical disks, on a DASD array, on magnetic tape, on a conventional hard disk drive, on electronic read-only memory or on electronic ransom access memory, or other appropriate data storage device. In an illustrative embodiment of the invention, the computer-executable instructions may be lines of compiled C++ language code.

It is to be understood that the present invention alternatively can be implemented by logic circuits (not shown). As yet another alternative, the present invention can be implemented by a circuit board (not shown), and the operative components of the control module 28 accordingly would be electronic components on the circuit board.

Returning to FIG. 1, the landfill 14 includes a plurality of gas extraction cells, generally designated 34. As shown, each cell 34 can include one or more gas extraction wells 36, with each well 36 including a respective vertically-oriented well casing 38 that is advantageously made of four inch or six inch diameter polyvinylchloride piping (4" or 6" PVC) that has a lower perforated segment 40 surrounded by washed gravel. Other size pipe, however, and other materials, e.g., high density polyethylene (HDPE), fiberglass, or steel, may be used. Further details of the wells 36 are disclosed in co-pending U.S. patent application Ser. No. 08/646,040, filed May 7, 1996 for an invention entitled "FLOW METERING DEVICE FOR LANDFILL GAS EXTRACTION WELL", assigned to the same assignee as the present invention and incorporated herein by reference.

As further shown in FIG. 1, a respective manually-operated inlet isolation valve HV1 is connected to each well 36 and to a respective flexible coupling 42, to establish gas communication between the coupling 42 and the well 36. Preferably, the inlet isolation valve HV1 is a type GVG-2000 valve made by KBI. In turn, each coupling 42 interconnects the associated inlet isolation valve HV1 to components within a concrete or fiberglass vault 44, as described below in reference to FIG. 2. Moreover, as shown in FIG. 1 each vault 44 receives pressurized air from an air compressor 46, and each vault 44 includes piping that is in fluid communication with a vacuum blower 48, for evacuating gas from the cells 34. In turn, the outlet of the blower 48 is connected to a burn-off flare or cogeneration plant flare 49 in accordance with principles well-known in the art to oxidize gases that are extracted from the landfill 14.

Additionally, components within each vault 44 receive power from the ac power supply 22, and vault 44 components also communicate with the field controller 24 and, hence, the computer 12, via an input data line 50 and an output data line 52. The data lines 50, 52 can be electrical conductors or optical fibers. It is to be understood, however, that the vaults 44 alternatively can communicate with the computer 12 via a radiofrequency (RF) link or satellite link, or other wireless link, if desired. In any event, as will become clearer in light of the disclosure below, the computer 12 can store and display feedback data from the vaults 44, including gas flow rate, flowing temperature, cell pressure (i.e., vacuum), oxygen concentration, methane concentration, carbon dioxide concentration, and control valve position.

Figure 2:
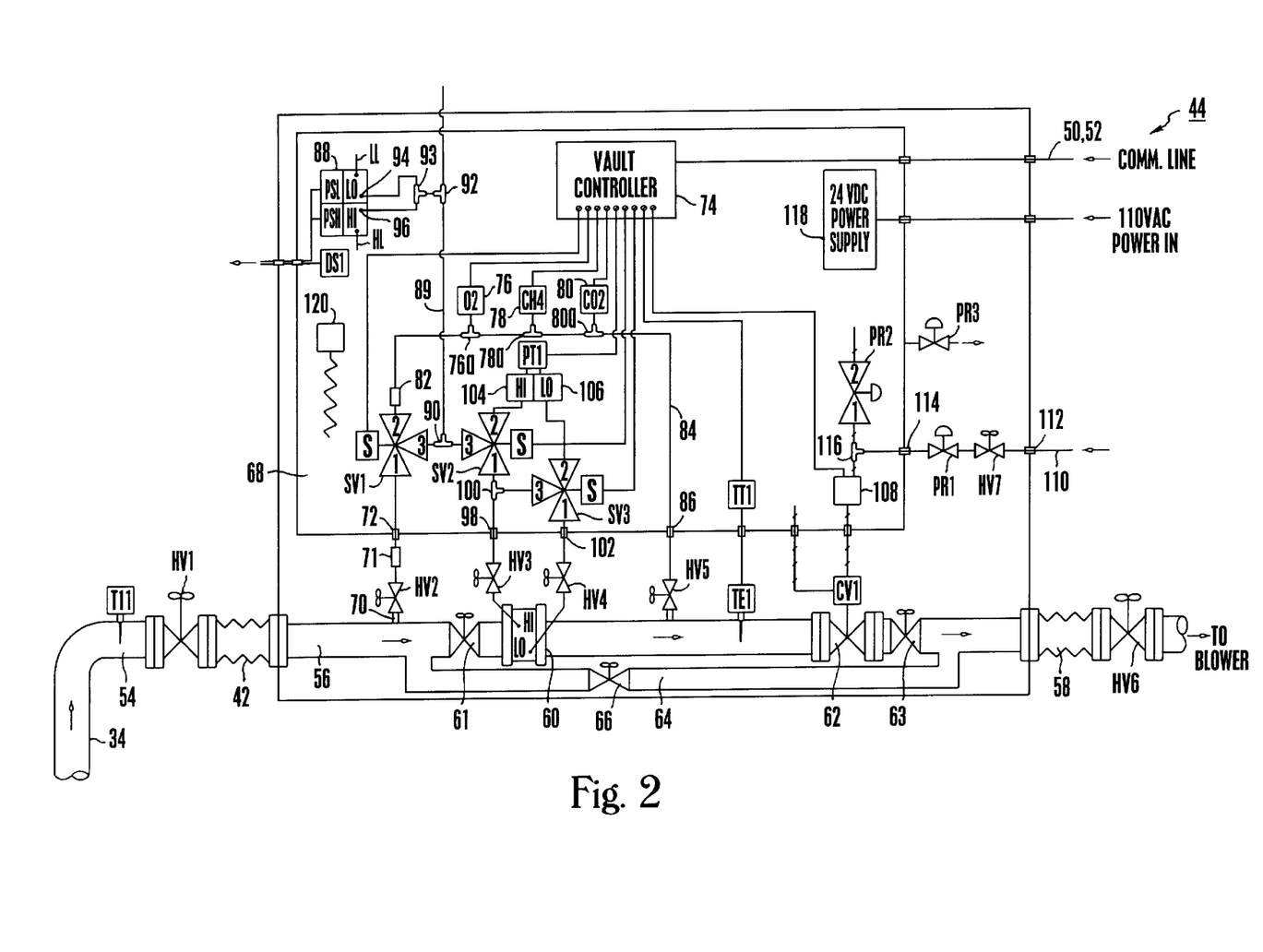
FIG. 2 is a schematic diagram of the components of a vault of the present invention.

FIG. 2 shows the details of a vault 44 of the present invention. As shown, the inlet isolation valve HV1 is connected to a lateral segment 54 of the cell 34. If desired, an inlet temperature sensor TI1 can be engaged with the lateral segment 54 for generating a signal representative of the temperature of the gas inside the lateral segment 54. As discussed above, the inlet isolation valve HV1 is connected to an inlet flexible coupling 42, which in turn is connected to a metering pipe 56 within the vault 44. The outlet of the metering pipe 56 is connected to the vacuum blower 48 (FIG. 1) via an outlet flexible coupling 58 and a manually-operated outlet isolation valve HV6.

As shown in FIG. 6, the metering pipe 56 includes a flow sensor, preferably an orifice assembly 60. The preferred embodiment of the orifice assembly 60 is fully disclosed in co-pending U.S. patent application Ser. No. 08/646,040, filed May 7, 1996 for an invention entitled "FLOW METERING DEVICE FOR LANDFILL GAS EXTRACTION WELL", assigned to the same assignee as the present invention and incorporated herein by reference. A manually-operated flow sensor isolation valve 61 is provided in the metering pipe 56 just upstream of the flow sensor 60 to isolate the flow sensor 60.

In addition to the orifice assembly 60, the metering pipe 56 includes a fluid flow control valve 62 for regulating the rate of gas flow through the metering pipe 56. In one embodiment, the control valve 62 is a pneumatically-operated valve made by Masonelfan or Ryan Herco, although in another embodiment the control valve 62 can be electrically operated. Accordingly, the control valve 62 includes a pneumatic operator CV1 which is operably associated with the gas extraction control system of the present invention for establishing a desired gas extraction rate from the cell 34. A manually-operated flow control valve outlet isolation valve 63 is provided in the metering pipe 56 just downstream of the control valve 62 as shown.

In the preferred embodiment, fluid flow can be shunted around the orifice assembly 60 and control valve 62 through an orifice bypass pipe 64. As the skilled artisan will appreciate, a bypass valve 66 is installed in the bypass pipe 64 for selectively establishing fluid flow through the bypass pipe 64. Accordingly, to bypass the flow sensor 60, the isolation valves 61, 63 are shut and the bypass valve 66 is opened.

FIG. 2 further shows that an instrument system is associated with each vault 44. Specifically, a pressurized enclosure 68, e.g., a type 70 SE enclosure made by InTerTec, is disposed in the vault 44, and the enclosure 68 houses a plurality of instruments and electrically-operated instrument valves. More specifically, an inlet gas concentration and vacuum sensing pipe 70 is in fluid communication with the metering pipe 56 upstream of the orifice assembly 60, and the inlet sensing pipe 70 extends into the enclosure 68 through a filter 71 and pipe seal fitting 72. A manually operated inlet concentration pipe isolation valve HV2 is installed in the inlet sensing pipe 70.

Inside the enclosure 68, an inlet regulating valve SV1 is installed in the inlet sensing pipe 70. As can be appreciated in reference to FIG. 2, the inlet regulating valve SV1 is a three-way solenoid valve having a sample inlet port "1", a sample outlet port "2", and an atmospheric inlet port "3". Additionally, the inlet regulating valve SV1 includes an associated solenoid "S" as shown, and the solenoid "S" is electrically connected to a vault controller 74, also located within the enclosure 68. The vault controller 74 is in communication with the computer 12 (FIG. 1). As more fully disclosed below, the vault controller 74 controls the solenoid "S" of the inlet regulating valve SV1 to establish fluid communication between the various ports of the valve SV1 as discussed further below. The inlet regulating valve SV1 can be a type 311-C-1/16-N-SS-1 valve made by Burkert, and the vault controller 74 can be a microprocessor 256 KB-2 MB controller marketed by Landfill Gas & Environmental, Inc.

It is to be understood that although the vault controller 72 undertakes its functions in response to the remote computer 12, it can operate independently of the computer 12. For example, the vault controller 74 can download commands from the computer 12, lose communication with the computer 12, and nonetheless continue the monitoring and control activities discussed below, storing data for subsequent transmission to the computer 12. Alternatively, the function of the computer 12 can be dispersed among the several vault controllers 74, with each cell 34 consequently being controlled independently of the other cells 34. Preferably, however, a single computer 12 controls the vault controllers 74 as described herein.

It can be appreciated in reference to FIG. 2 that the sample inlet port "1" of the inlet regulating valve SV1 can be connected to the sample outlet port "2" to thereby establish fluid communication between the metering pipe 56 and first through third gas concentration sensors 76, 78, 80. As shown in FIG. 2, gas from the sample outlet port "2" passes through a filter 82 and thence to three "T" connections 76a, 78a, 80a, each one being associated with a respective one of the first through third gas concentration sensors 76, 78, 80. The filter 82 can be a particulate filter made by ITT Barton.

As indicated in FIG. 2, the first gas concentration sensor 76 is an oxygen sensor, while the second gas concentration sensor 78 is a methane sensor. In contrast, the third gas concentration sensor 80 is a carbon dioxide sensor. The gas concentration sensors 76, 78, 80 respectively generate electrical signals representative of oxygen, methane, and carbon dioxide concentration of the gas from the cell 34 being extracted through the metering pipe 56. It can be readily seen in FIG. 2 that the gas concentration sensors 76, 78, 80 are electrically connected to the controller 74 for sending respective feedback signals thereto, and from thence to the computer 12 (FIG. 1). The gas concentration sensors 76, 78, 80 can be suitable sensors made by QEL or by ITT Barton.

To complete the path for fluid flow, an outlet gas concentration and vacuum sensing pipe 84 is connected to the third "T" fitting 80a and extends through a pipe seal fitting 86 to the metering pipe 56 at a location downstream of the orifice assembly 60. A manually operated outlet gas concentration and vacuum pipe isolation valve HV5 is installed in the outlet sensing pipe 84. The outlet gas concentration and vacuum pipe isolation valve HV5 can be a type 1076002 valve made by Harrington. With this structure, when the isolation valves HV2 and HV5 are open, the pressure drop across the orifice assembly 60 drives gas through the sensing pipes 70, 84 for sampling of the gas by the gas concentration sensors 76, 78, 80.

The present invention also provides for purging the gas sensors 76, 78, 80. Specifically, the controller 74 can cause the sample inlet port "1" of the regulating valve SV1 to close and the sample outlet port "2" to communicate with the atmospheric inlet port "3". With this configuration of the valve SV1, fluid communication is established between sensors 76, 78, 80 and the atmosphere external to the vault 44 via a purge line 89 and two "T" fittings 90, 92, to thereby direct external air to the sensor 76, 78, 80.

Furthermore, the purge line 89 can be used to send an atmospheric pressure reference signal to a pressure sensor 88 via the "T" fitting 92 and a "T" fitting 93. More particularly, atmospheric pressure is sensed via the purge line 89 and "T" fittings 92, 93 by a low pressure sensor 94 and a high pressure sensor 96, both of which are exposed via respective lines "LL" and "HL" to ambient pressure within the enclosure 68. If desired, the low and high pressure sensors 94, 96 can be separate pressure sensors, the electrical circuits of which are connected in series.

When pressure in the enclosure 68 falls below a predetermined low pressure alarm setpoint, a low pressure alarm switch "PSL" associated with the low pressure sensor 94 generates a low pressure signal and sends the signal to the controller 74 and thence to the computer 12 via the field controller 24 (FIG. 1). On the other hand, when pressure within the enclosure 68 exceeds a predetermined high pressure alarm setpoint, a high pressure alarm switch "PSH" that is associated with the high pressure sensor 96 generates a high pressure signal and sends the signal to the field controller 24. Further, the enclosure 68 includes an access door (not shown), and a door switch DS1 generates a door open alarm signal when the access door is not fully shut. As can be appreciated in reference to FIG. 2, the door open alarm signal is sent to the field controller 24. The circuits of the low and high pressure switches 94, 96 and the door switch DS1 can be connected in series, such that if any one of the low pressure, high pressure, or door open signals are generated, an alarm is activated. The low pressure alarm switch "PSL" can be a type 1823-00 switch made by Dwyer Instruments, whereas the high pressure alarm switch "PSH" is a type 1823-5 switch made by Dwyer Instruments.

Turning to the instrumentation associated with the orifice assembly 60, the high pressure (i.e., upstream) port of the assembly 60 is connected to a high side regulating three-way solenoid valve SV2 within the enclosure 68 via a high side isolation valve HV3, a pipe seal fitting 98, and a "T" fitting 100. The high side regulating three-way solenoid valve SV2 can be a type B-24/DC-08-Z-H-000 valve made by Burkert. In contrast, the low pressure (i.e., downstream) port of the assembly 60 is connected to a low side regulating three-way solenoid valve SV3, e.g., a type B-24/DC-08-Z-H-000 valve made by Burkert, within the enclosure 68 via a low side isolation valve HV4 and a pipe seal fitting 102. The low side isolation valve HV4 can be a type 1080002 valve made by Harrington.

It is to be understood that the high and low side regulating valves SV2 and SV3 are controlled by the vault controller 74. Accordingly, the regulating valves SV2 and SV3 can be configured to direct gas from their respective inlet ports "1" to respective flow metering outlet ports "2", and thence to opposed high and low sides 104, 106 of a differential pressure meter PT1. The differential pressure meter PT1 generates a flow rate feedback signal representative of gas flow rate through the metering pipe 56, and this signal is sent to the vault controller 74 as shown, and thence to the computer 12. In one embodiment, the pressure meter PT1 is a differential pressure meter made by Dwyer Instruments. If desired, the regulating valves SV2 and SV3 can be configured to direct gas from their respective inlet ports "1" to respective equalizing outlet ports "3", to equalize pressure on both sides of the differential pressure meter PT1 for, e.g., testing and diagnostics.

In addition to the gas sampling and flow measuring pathways described above, vacuum within the metering pipe 56 (relative to atmospheric pressure) can be sensed. More specifically, the controller 74 can cause the inlet port "1" of the high side solenoid valve SV2 to close, and the ports "2" and "3" of the high side valve SV2 to communicate with each other, such that atmospheric pressure is presented to the high side 104 of the pressure meter PT1 through the purge line 89. Then, the inlet port "1" of the low side valve SV3 is closed, and the ports "2" and "3" of the low side valve configured to communicate with each other, such that pressure from the high side port of the flow meter assembly 60 is presented to the low side 106 of the pressure meter PT1 through the high side isolation valve HV3. Consequently, the signal generated by the pressure meter PT1 is representative of vacuum pressurer within the metering pipe 56.

If desired, a temperature sensor TE1 can be engaged with the metering pipe 56 downstream of the orifice assembly 60. The temperature sensor TE1 generates a signal representative of fluid temperature within the metering pipe 56 adjacent the sensor TE1, and then sends this signal to a temperature transmitter TT1. As shown in FIG. 2, the temperature transmitter TT1 is located within the pressurized enclosure 68, and is electrically connected to the vault controller 74 for sending the temperature signal to the vault controller 74. The temperature sensor TE1 can be a resistance temperature detector (RTD) made by CFM, and the temperature transmitter TT1 can also be made by CFM.

Continuing with the description of FIG. 2, the pneumatic actuator CV1 of the flow control valve 62 is connected to an electrically operated pilot valve 108, e.g., a type X55-600-GP-1-SM valve made by Ronan. The pilot valve 108 is electrically connected to the vault controller 74 for control of the pilot valve 108 (and, hence, control valve 62) by the vault controller 74, in response to the computer 12 logic disclosed below.

Actuating air from the compressor 46 (FIG. 1) is supplied to the control valve 62 via the pilot valve 108. Specifically, an actuating air pipe 110 is in fluid communication with the compressor 46, and the actuating air pipe 110 extends through a pipe seal fitting 112 into the vault 44. A manually operated actuating air isolation valve HV7 is installed in the actuating air pipe 110 as shown.

Downstream of the actuating air isolation valve HV7 is a pressure regulating valve PR1. Per the present invention, the pressure regulating valve PR1 reduces the actuating air pressure as appropriate for operating the control valve 62. The actuating air pipe 110 extends from the pressure regulating valve PR1 through a pipe seal fitting 114 into the enclosure 68.

As shown in FIG. 2, the actuating air pipe 110 terminates in a "T" fitting 116. Air is directed through the "T" fitting 116 to the pilot valve 108 and through an enclosure pressure regulating valve PR2. As intended by the present invention, the pressure regulating valve PR2 reduces the pressure of air from the "T" fitting 116 as appropriate to maintain the air pressure within the enclosure 68 slightly above ambient pressure. Consequently, potentially flammable gas is prevented from leaking into the enclosure 68 and being ignited by the electrical components therein. To avoid overpressurizing the enclosure 68, a bulkhead pressure relief valve PR3 opens to port air from the enclosure 68 into the vault 44 when the pressure within the enclosure 68 exceeds a predetermined high pressure relief setpoint that is higher than the high pressure alarm setpoint disclosed above. In the present embodiment, the pressure regulating valves PR1, PR2, PR3 are made by Bellofram.

Additionally, as indicated above actuating air from the "T" fitting 116 is sent to the pilot valve 108. The vault controller 74 controls the flow of actuating air through the pilot valve 108 and, hence, controls the control valve 62. By appropriately controlling the control valve 62, the vault controller 74 controls the gas flow rate through the cell 34 as appropriate to accord with a user-selected one of the control regimes described below.

Completing the description of FIG. 2, the vault controller 74 is electrically connected to the computer 12 (FIG. 1) via the data lines 50, 52 (shown as a single conduit in FIG. 2). Also, the ac power supply 22 (FIG. 1) is connected to a dc power supply 118 within the enclosure 68. Preferably, the dc power supply 118 transforms ac power to twenty four volt direct current (24 vDC) power. It is to be understood that the dc power supply 118 is electrically connected to the electrical components within the enclosure 68 in accordance with well-known principles to energize the components. If desired, a heater 120, preferably made by Chromalox, can be disposed within the enclosure 68 to heat the enclosure 68 in cold weather.

Now referring to FIGS. 3 and 4, the operation of the flow control strategy regime of the control module 28 (FIG. 1) of the present invention can be seen. As disclosed below, the flow control regime shown in FIGS. 3 and 4 seeks to maintain a constant predetermined gas flow rate from each cell 34 independently of the other cells, or to maintain a constant predetermined global gas flow rate for the entire landfill 14, within oxygen, vacuum, and temperature safety constraints. If desired, as disclosed in detail in reference to FIG. 4, the flow rates from the cells 34 can be further adjusted to maximize methane extraction from the landfill 14, or to minimize oxygen extraction from the landfill 14.

Commencing at decision diamond 150 in FIG. 3, the module 28 determines whether a global flow rate setpoint has been selected by the operator. If not, the logic proceeds to block 152, wherein the desired flow rate ($QW_i$) for each cell 34 is established by the operator.

On the other hand, if the operator has indicated that a single global flow rate (QF) is to be established, the logic proceeds to block 154, wherein the operator defines the global flow rate. From block 154, the logic proceeds to block 156, wherein the flow rate for each cell is established by dividing the global flow rate by a weighting factor for the particular cell 34. This weighting factor can be empirically determined and set by the operator based on the number of cells 34 in the landfill 14, and/or, as disclosed further below, it can be established by the system 10 to maximize methane extraction or to minimize oxygen extraction from the landfill 14. In any case, the total gas extraction rate from the landfill 14 is established to be less than the gas burn rate, i.e., the capacity of, the flare 49 (FIG. 1).

In light of the above discussion, it is to be understood that the logic divulged below can apply to each cell 34, if each cell 34 is to be controlled independently of the other cells, or it can represent logic undertaken for the entire landfill 14. Thus, for example, at decision block 158, to which the logic proceeds from either block 152 or block 156, it is determined whether the oxygen content of the gas being extracted from the cell (if each cell is being separately controlled) exceeds a setpoint for that cell, or whether the cumulative oxygen content of the gas being extracted from the landfill 14 (if a global flow rate has been enabled) exceeds a global oxygen setpoint. Likewise, the below-disclosed logic related to vacuum and temperature can be applied to each cell 34 independently or to the cells 34 as a single unit. It is to be further understood that while, for ease of disclosure, the logic described below sequentially tests for high oxygen, then high vacuum, then high temperature, the present invention contemplates continual (i.e., parallel) monitoring of these attributes.

If the test at decision diamond 158 is positive, the logic moves to decision diamond 160, wherein it is determined whether a stabilization time period has elapsed from the time at which the determination at decision diamond 158 was made. As shown in FIG. 3, the logic loops between decision diamonds 158, 160 until the stabilization period has elapsed. When the stabilization period has elapsed, the logic moves to block 162 to reduce the signal (MV) to the control valve of the cell under test (or control valves of the cells, if a global strategy has been invoked) by, e.g., one percent as indicated in FIG. 3.

Moving to decision diamond 164, the logic determines whether the oxygen content has been reduced to under a predetermined fraction, e.g., 95%, of the oxygen setpoint. If not, the process loops back to decision diamond 158. Otherwise, from decision diamond 158 or 164 when the test there is negative, the logic moves to decision diamond 166.

At decision diamond 166, it is determined whether the measured vacuum "V" (from each cell 34 or from the landfill 14, as appropriate) exceeds a predetermined vacuum setpoint ($V_H$). If the test at decision diamond 166 is positive, the logic moves to decision diamond 168, wherein it is determined whether a stabilization time period has elapsed from the time at which the determination at decision diamond 166 was made. As shown in FIG. 3, the logic loops between decision diamonds 166, 168 until the stabilization period has elapsed. When the stabilization period has elapsed, the logic moves to block 170 to reduce the signal (MV) to the control valve of the cell under test (or control valves of the cells, if a global strategy has been invoked) by, e.g., one percent as indicated in FIG. 3.

Moving to decision diamond 172, the logic determines whether the vacuum is in a predetermined fractional range, e.g., 85%–95%, of the vacuum setpoint. If not, the process loops back to decision diamond 166. Otherwise, the logic moves to decision diamond 174, wherein it is determined whether the measured flow rate (QW) is less than the desired flow rate ($QW_t$). If it is, the logic sets the predetermined vacuum setpoint $V_H$ to be the measured vacuum V at block 176. From block 176, or from decision diamonds 172, 174 if the tests there were negative, the process loops back to decision diamond 166.

Once vacuum has been satisfactorily adjusted as disclosed above, as indicated by a negative test at decision diamond 166, the logic can, if desired, move to decision diamond 178, wherein it is determined whether the temperature of the gas exceeds a temperature setpoint. If temperature is too high, the logic moves to decision diamond 180, wherein it is determined whether a stabilization time period has elapsed from the time at which the determination at decision diamond 178 was made. As shown in FIG. 3, the logic loops between decision diamonds 178, 180 until the stabilization period has elapsed. When the stabilization period has elapsed, the logic moves to block 182 to shut the control valve of the cell under test, or to shut the control valves of all the cells if the test point it the cumulative gas flow from the entire landfill 14. The logic then exits.

If it is determined at decision diamond 178 that gas flow temperature is satisfactory, the logic proceeds to decision diamond 184, wherein it is determined whether oxygen minimization and/or methane maximization has been enabled. If not, the above-described process continues. If, on the other hand, oxygen minimization and/or methane maximization have been enabled, the logic proceeds to undertake the steps shown in FIG. 4.

FIG. 4 shows the logic of the module 28 in minimizing the extraction of oxygen or maximizing the extraction of methane from the landfill 14, in conjunction with the flow control strategy shown in FIG. 3. As indicated at block 190, when methane maximization or oxygen minimization is enabled, the single flow rate setpoint is replaced by an operator-defined field flow rate setpoint range from a minimum desired flow rate $QF_L$ to a maximum desired flow rate $QF_H$.

At decision diamond 192, it is determined whether the methane maximization regime has been enabled. If not, the logic moves to decision diamond 194 to determine whether the oxygen minimization regime has been enabled, and if not, the logic returns to the main flow control strategy shown in FIG. 3.

If, however, it is determined at decision diamond 192 that the methane minimization regime has been enabled, the control valve(s) to the cell(s) 34 that have the highest methane content are incrementally opened, to thereby incrementally increase the gas flow from those cells, at block 196. Then, at decision diamond 198, it is determined whether the measured field flow rate $QF_i$ (i.e., the measured total flow rate from the landfill 14, as indicated by the combined signals from the flow meters of the cells 34) exceeds the maximum desired flow rate $QF_H$. If it does, at block 200 the logic incrementally closes the control valve(s) to the cell(s) 34 that have the lowest methane content, to thereby incrementally decrease the gas flow from those cells.

From block 200 or from decision diamond 198 if the test there was negative, the logic moves to decision diamond 202, wherein it is determined whether the measured field flow rate $QF_i$ is less than the minimum desired flow rate $QF_L$. If the measured field flow rate $QF_i$ is more than the minimum desired flow rate $QF_L$, the logic proceeds to decision diamond 204. At decision diamond 204, it is determined whether the methane extraction rate from the landfill 14 exceeds a predetermined maximum threshold, and if it does not, the logic proceeds to state 206 to conduct the next test cycle. Otherwise, the landfill field is shut down by closing all of the control valves to the cells 34 at block 208. Likewise, if it is determined at decision diamond 202 that the measured field flow rate $QF_i$ is less than the minimum desired flow rate $QF_L$, the landfill 14 is shut down at block 208.

Continuing with the description of the methane maximization logic shown in FIG. 4, the logic moves from block 208 to decision diamond 210, wherein it is determined whether automatic restart of the landfill 14 field has been enabled. If not, the logic proceeds to state 206 to await the next cycle, which next cycle is deferred until the landfill 14 has been manually restarted.

On the other hand, if automatic landfill 14 restart has been enabled, the logic moves to decision diamond 212, and remains in a loop as shown between decision diamonds 212 and 210 until a predetermined restart time period has elapsed. During the restart time period, audible and visual alarms may be activated, if desired, to alert landfill 14 personnel of the impending automatic restart of the landfill 14. When the restart period has elapsed, the logic moves to block 214 to reopen the control valves to thereby restart the gas extraction process from the landfill 14.

Recall that at decision diamond 194 it is determined whether the oxygen minimization regime of the present invention has been enabled. If it has, the logic proceeds to decision diamond 216, wherein it is determined whether the measured field flow rate $QF_i$ exceeds the minimum desired flow rate $QF_L$. If it does, at block 218 the logic incrementally closes the control valve(s) to the cell(s) 34 that have the highest oxygen content, to thereby incrementally decrease the gas flow from those cells.

From block 218, the logic proceeds to decision diamond 220, wherein it is again determined whether the measured field flow rate $QF_i$ exceeds the minimum desired flow rate $QF_L$. If it does, the logic loops back to block 218 to incrementally close the control valve(s) to the cell(s) 34 that have the highest oxygen content. Thus, the present oxygen minimization strategy regime seeks to minimize the rate of oxygen withdrawal from the landfill 14, while nevertheless maintaining the total gas extraction rate from the landfill 14 above a predetermined threshold.

When it is determined at either decision diamond 216 or decision diamond 220 that the measured field flow rate $QF_i$ does not exceed the minimum desired flow rate $QF_L$, the logic moves to block 222 to incrementally open the control valves to the cells 34 having the lowest oxygen content, to thereby increase the gas flow from these cells. Then, at decision diamond 222 the logic determines whether the measured field flow rate $QF_i$ exceeds the minimum desired flow rate $QF_L$, and if not loops back to block 222 to incrementally increase flow from low-oxygen cells 34.

Otherwise, the logic moves to decision diamond 226 to determine whether the oxygen content from each cell 34 is equal to the oxygen content of all other cells 34. If the oxygen content is not the same for all cells 34, the logic loops back to block 218. In contrast, if the oxygen content is the same for all cells 34, the logic moves to decision diamond 228 to determine whether the total oxygen extraction rate for the landfill 14 is greater than a predetermined threshold, and whether the measured field flow rate $QF_i$ is about equal to the minimum desired flow rate $QF_L$. Such a condition would indicate that the oxygen extraction rate from the landfill 14 cannot be reduced below the threshold, while maintaining the total gas extraction rate above the minimum desired flow rate $QF_L$. Accordingly, if the test at decision diamond 228 is positive, the logic moves to block 208 to shut down gas extraction from the landfill 14 as described previously. If, however, it is determined at decision diamond 216 that either the total oxygen extraction rate for the landfill 14 is less than the predetermined threshold, or that the measured field flow rate $QF_i$ is greater than the minimum desired flow rate $QF_L$, the logic moves to state 206 to conduct the next test cycle.

Now referring to FIG. 5, an alternate control strategy of the present invention, one based on maintaining a predetermined vacuum pressure either in each cell 34 individually or at the blower 48 (FIG. 1), can be seen. It is to be understood that when overall system 10 vacuum, that is, the vacuum at the blower 48, is being controlled, a pressure transducer (not shown) that is in all essential respects identical in construction and operation to the pressure meter PT1 shown in FIG. 2 is in fluid communication with the blower 48 and in data communication with the computer 12. For purposes of disclosure, the logic shown in FIG. 5 is for controlling vacuum in a single cell 34.

Commencing at block 230, a desired vacuum $V_0$ and maximum vacuum $V_{max}$ are established by the operator of the system 10. Then, at decision diamond 232 it is determined whether the measured vacuum V is less than the desired vacuum $V_0$. If it is, the logic moves to block 234 to incrementally open the control valve associated with the cell 34. At decision diamond 236, it is determined whether the operation performed at block 234 had the desired effect, i.e., whether the measured vacuum V is at least as great as the desired vacuum $V_0$. If it isn't, the logic loops back to block 234, but otherwise the logic proceeds to decision diamond 238. Also, if it is determined at decision diamond 232 that the measured vacuum V is at least equal to the desired vacuum $V_0$, the logic moves to decision diamond 238.

At decision diamond 238, it is determined whether the measured vacuum V is greater than the maximum vacuum $V_{max}$. If the measured vacuum V is not greater than the maximum vacuum $V_{max}$, the logic moves to decision diamond 240, wherein it is determined whether the measured oxygen extraction rate from the cell 34 is greater than a predetermined threshold $O_{2max}$. If it is determined at decision diamond 240 that the oxygen extraction rate is within specification, the logic moves to decision diamond 242, to determine whether the measured temperature of the flowing gas is greater than a predetermined threshold "$temp_{max}$". If temperature is within specification, the logic loops back to decision diamond 232 as shown.

If, however, any one of the tests at decision diamonds 238, 240, 242 is positive, i.e., if it is determined that vacuum, temperature, or oxygen extraction rate is too high, the logic moves to block 244. At block 244, the module 28 of the computer 12 returns a signal indicating that a safety setpoint has been violated, and that field integrity consequently has been potentially compromised. At block 244 the landfill field is accordingly shut down and restarted as described previously with respect to the flow control regime shown in FIGS. 3 and 4.

While the particular LANDFILL GAS FLOW CONTROL SYSTEM as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A landfill gas extraction system for controlling the extraction of gas from a landfill having a plurality of gas well cells, each cell including one or more gas wells, and a source of vacuum in fluid communication with the cells, comprising:
   at least one landfill sensor mounted in a pipe attached to a well, the sensor generating a signal representative of a parameter within the pipe and the well;
   a computer receiving signals from at least the sensor and generating control signals in response thereto; and
   a plurality of computer-responsive control valves, each control valve being in fluid communication with a respective cell, each control valve being configured for incremental control thereof based on control signals from the computer for controlling gas extraction from the cell, such that plural flow rates can be established through the control valves as determined by the computer based on the signals from the sensor.

2. The system of claim 1, further comprising, for each cell, at least one sensor for generating a feedback signal representative of a parameter from the group consisting of: pressure, temperature, flow rate, oxygen concentration, methane concentration, and carbon dioxide concentration, wherein the feedback signal is communicated to the computer and the computer controls the respective control valve in response thereto.

3. The system of claim 2, wherein the sensor is a flow rate sensor and the feedback signal represents flow rate through the cell, and the computer controls the respective control valve to establish a predetermined flow rate.

4. The system of claim 3, wherein the predetermined flow rate through each cell is based on a predetermined landfill total flow rate.

5. The system of claim 3, further comprising, for each cell, a pressure sensor for generating a vacuum signal representative of pressure in the cell, and the computer includes computer readable code means for comparing the vacuum signal to a predetermined vacuum setpoint and controlling the control valve in response thereto.

6. The system of claim 5, further comprising, for each cell, an oxygen sensor for generating an oxygen signal representative of oxygen concentration in the cell, and the computer includes computer readable code means for comparing the oxygen signal to a predetermined oxygen setpoint and controlling the control valve in response thereto.

7. The system of claim 2, wherein the sensor is a pressure sensor and the feedback signal represents vacuum pressure in the cell, and the computer controls the control valve of each cell to establish a predetermined vacuum pressure.

8. The system of claim 7, further comprising, for each cell, an oxygen extraction sensor for generating an oxygen extraction signal representative of oxygen extraction from the cell, and the computer includes computer readable code means for comparing the oxygen extraction signal to a predetermined oxygen extraction setpoint and controlling the control valve in response thereto.

9. The system of claim 8, further comprising, for each cell, a temperature sensor for generating a temperature signal representative of gas temperature in the cell, and the computer includes computer readable code means for comparing the temperature signal to a predetermined setpoint and controlling the control valve in response thereto.

10. The system of claim 3, further comprising an oxygen sensor for generating an oxygen feedback signal, and the computer controls the control valve of each cell to maintain oxygen concentration below a predetermined oxygen concentration setpoint.

11. The system of claim 10, wherein the computer includes computer readable code means for controlling the control valves such that the sum of the gas flow rates through all the cells is maintained within a predetermined field flow rate range.

12. The system of claim 3, further comprising a methane sensor for generating a methane signal, wherein the computer controls the control valve of each cell in response to the methane signal.

13. The system of claim 12, wherein the computer includes computer readable code means for controlling the control valves such that the sum of the gas flow rates through all the cells is maintained within a predetermined field flow rate range, and wherein the computer causes relatively more gas to be extracted from cells having relatively high methane concentrations.

14. The system of claim 2, further comprising a respective vault for holding each control valve, each vault including a respective pressurized enclosure for holding the sensor therein with the control valve being external to the enclosure, wherein the control valve is a pneumatically-operated valve.

15. The system of claim 14, further comprising a vault controller disposed in the enclosure, the vault controller being in communication with the computer.

16. The system of claim 15, further comprising a solenoid valve disposed in the enclosure and electrically connected to the vault controller for control of the solenoid valve to selectively isolate the sensor, whereby a positive pressure is maintained within the enclosure to prevent the flow of gas into the enclosure, and whereby no electrically-powered components of the vault are located outside the enclosure.

17. A computer program device comprising:
    a computer program storage device readable by a digital processing system; and
    a computer program on the program storage device and including instructions executable by the digital processing system for performing method steps for controlling at least one computer-responsive valve disposed in a landfill cell gas extraction well to thereby control gas extraction from the pipe, the method steps comprising:
        receiving a feedback signal from a well representative of at least one of: gas pressure inside the well, gas flow rate through the well, oxygen concentration of gas inside the well; and
        incrementally moving the valve in response thereto, such that plural flow rates can be established through the control valves as determined by the computer based on the feedback signal from the well.

18. The device of claim 17, wherein the method steps further comprise moving the valve in response to methane concentration in the pipe.

19. The device of claim 18, wherein the method steps further comprise:
    determining a desired gas flow rate through the pipe based on the number of wells in the landfill and at least one of: landfill flare capacity, methane concentration in the pipe.

* * * * *